United States Patent [19]

Manzer et al.

[11] Patent Number: 5,302,765
[45] Date of Patent: * Apr. 12, 1994

[54] CATALYTIC PROCESS FOR PRODUCING $CF_3CHCLF$

[75] Inventors: Leo E. Manzer; V. N. Mallikarjuna Rao; Frank J. Weigert, all of Wilmington, Del.

[73] Assignee: E. I. Du Pont de Nemours and Company, Wilmington, Del.

[*] Notice: The portion of the term of this patent subsequent to Jun. 9, 2009 has been disclaimed.

[21] Appl. No.: 892,064

[22] Filed: May 29, 1992

[51] Int. Cl.$^5$ .............................................. C07C 17/00
[52] U.S. Cl. .................................................... 570/123
[58] Field of Search ......................................... 570/123

[56] References Cited

U.S. PATENT DOCUMENTS

| | | |
|---|---|---|
| 2,644,845 | 7/1953 | McBee . |
| 4,490,534 | 12/1984 | Fujikawa et al. . |
| 4,996,379 | 2/1991 | Oshio et al. . |
| 5,120,883 | 6/1992 | Rao et al. . |
| 5,171,899 | 12/1992 | Furutaka et al. .................. 570/123 |

FOREIGN PATENT DOCUMENTS

| | | |
|---|---|---|
| 3-58946 | 3/1991 | Japan . |
| 1225956 | 1/1969 | United Kingdom . |
| 1578933 | 5/1977 | United Kingdom . |

OTHER PUBLICATIONS

Chem. Abst. 87(10) 68874q.
A. A. Goleva et al., Russ. J. Phys. Chem., 44$^2$, 290–1 (1970).
M. Biswas et al., J. Macromol. Sci., Chem., A20(8), 861–76 (1983).
Chem. Abst. 80(25) 145470q.
Chem. Abst. 80(25) 145469w.
Organic Synthesis, Collective vol. 3 pp. 685–690.
J. W. Hassler, "Activated Carbon", pp. 344–345.
M. Smisek et al., "Active Carbon", pp. 61–70.
F. J. Long et al., "The Effect of Specific Catalysts on the Reactions of the Steam-Carbon System", Proc. Roy. Soc. (1952) pp. 100–110.
R. B. Anderson et al., "Surface Complexes on Charcoal", J. Phys. Colloid Chem., 51, pp. 1308–1329.
H. M. Frey, "A New Type of Catalytic Effect in the Oxidation of Carbon", Proc. Roy. Soc. (1055), pp. 510–518.
A. Blackburn et al., "Adsorption from Binary Liquid Mixtures: Some Effects of Ash in Commercial Charcoal" J. Chem. Soc. (1955), pp. 4103–4106.
F. J. Long et al., "The Catalysis of the Oxidation of Carbon", J. Chem. Phys., 47, pp. 361–378 (1950).

*Primary Examiner*—Alan Siegel

[57] ABSTRACT

A catalyic process is disclosed for producing $CF_3CHClF$ from $CF_3CH_2F$ by chlorination at elevated temperature. Suitable catalysts for the process include carbon catalysts and catalysts wherein halides of certain metals (La, Zn, Cu, Cr, Ru, Rh, and/or Pt) are supported on carbon.

17 Claims, No Drawings

CATALYTIC PROCESS FOR PRODUCING CF₃CHCLF

FIELD OF THE INVENTION

This invention relates to the chlorination of aliphatic hydrofluorocarbons and more particularly to catalytic chlorination of hydrofluorocarbons.

BACKGROUND

British Patent Specification 1,225,956 discloses a process for the production of a chlorofluoroethane of the general formula $CH_{3-n}Cl_nCClF_2$ where n is 0 to 3 comprising the photochemical chlorination of 1,1-difluoroethane, which may contain less than 2% HF.

There has been considerable interest in processes for the chlorination of aliphatic hydrofluorocarbons and hydrochlorofluorocarbons which avoid using expensive actinic light to effect such chlorination.

U.S. Pat. No. 4,490,534 discloses a process for the preparation of 3-chloro-5-trifluoromethylpyridine derivatives comprising reacting a 5-trifluoromethylpyridine having a hydrogen atom at the 3-position with chlorine in the presence of a catalyst selected from the group consisting of activated carbon and a chloride of a metal selected from the group consisting of iron, antimony, copper and zinc.

Many processes have been disclosed for the preparation 2-chloro-1,1,1,2-tetrafluoroethane (i.e., HCFC-124 or $CF_3CHClF$) and of 1,1,1,2-tetrafluoroethane (i.e., HFC-134a or $CF_3CH_2F$) which are useful refrigerants, propellants, and starting materials for producing various other halogenated hydrocarbons. 2,2-Dichloro-1,1,1,2-tetrafluoroethane (i.e., CFC-114a or $CCl_2FCF_3$) is a chlorofluorocarbon which has been used as an intermediate for the preparation of HCFC-124 and HFC-134a. More particularly, CFC-114a can be converted to HFC-134a as the major product and HCFC-124 as a minor product, by catalytic hydrogenolysis. HCFC-124 has also been prepared by the addition of HF to halogenated olefins and by the reaction of 2,2-dichloro-1,1,1-trifluoroethane with HF. HCFC-124 is also useful as a heat pump working fluid and as a blowing agent. There is interest in developing efficient methods of producing $CF_3CHClF$.

SUMMARY OF THE INVENTION

The present invention provides a process for producing 2-chloro-1,1,1,2-tetrafluoroethane comprising the step of contacting gaseous $CF_3CH_2F$ and chlorine with a catalyst at a temperature of from about 150° C. to about 450° C., the catalyst being selected from the group consisting of carbon catalysts and catalysts of a metal halide supported on carbon wherein the metal halide is selected from the group consisting of lanthanum chloride, lanthanum fluoride, zinc chloride, zinc fluoride, copper chloride, copper fluoride, chromium chloride, chromium fluoride, ruthenium chloride, ruthenium fluoride, rhodium chloride, rhodium fluoride, platinum chloride, platinum fluoride, and mixtures thereof.

DETAILS OF THE INVENTION

The present invention provides a process for the catalytic chlorination of $CH_2FCF_3$. Preferably, 1,1,1,2-tetrafluoroethane is converted to 2-chloro-1,1,1,2-tetrafluoroethane as the major product without isomerization or disproportionation.

The catalyst for the chlorination may be composed of carbon catalysts (e.g., activated carbon) alone or carbon with a chloride and/or fluoride of a metal selected from the group consisting of lanthanum, zinc, copper, chromium, ruthenium, rhodium, platinum and mixtures thereof. Under reaction conditions the metal halides may be in the form of mixed metal halides (e.g., a chlorofluoride).

Catalyst compositions consisting essentially of carbon are preferred and are considered particularly effective for chlorination. The carbon can be either washed or unwashed. Washing can be done with either water or acid. Washing, particularly with acids, reduces the ash content. Preferred acid-washed carbons contain 0.5 percent by weight or less, ash. Examples of acids which may be used in an acid wash include organic acids (e.g., acetic acid) and inorganic acids (e.g., HCl or $HNO_3$). Preferably hydrochloric acid or nitric acid is used. The acid treatment may be accomplished in several ways. A preferred embodiment is described as follows.

An activated carbon is soaked overnight with gentle stirring in a 1M solution of the acid prepared in deionized water. The carbon support is separated and washed with deionized water until the pH of the washings is about 3. The carbon support is then soaked again with gentle stirring in a 1M solution of the acid prepared in deionized water for about 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C. A sample of this washed carbon is then soaked, if desired, in 1M HF prepared in deionized water for about 48 hours at room temperature with occasional stirring in an HF resistant container. The carbon support is separated and washed repeatedly with deionized water until the pH of the washings is greater than 4. The carbon support is then dried at about 150° C., followed by calcination at about 300° C. prior to its use.

Commercially available carbons useful in the process of this invention include those sold under the following trademarks: Darco ™, Nuchar ™, Columbia SBV ™, Columbia MBV ™, Columbia MBQ ™, Columbia JXC ™, Columbia CXC ™, Calgon PCB ™, and Barnaby Cheny NB ™. Preferred carbons include those prepared from plant-based materials that have been twice treated with acid, as described above, to reduce the ash content. The carbon support can be in various forms (e.g., powder, granules, or pellets).

If the catalyst composition contains one or more metals selected from lanthanum, zinc, copper, chromium, ruthenium, rhodium and platinum, the percentage of metal in the catalyst composition is not considered critical. Typically, the metal content is from about 0.1% to 30% by weight of the carbon.

In accordance with this invention, gaseous $CH_2FCF_3$ and chlorine are contacted with the catalyst at elevated temperature to produce $CHClCF_3$. $CCl_2FCF_3$ may also be produced. An inert diluent such as argon, helium, nitrogen or $CCl_2FCF_3$ may be used in the chlorination reaction of the present invention. HF may also be present, particularly where catalysts consisting essentially of carbon are used. The amount of chlorine is not critical but is usually from 0.5 to 10 moles, preferably from 0.5 to 1 mole, per mole of $CH_2FCF_3$ starting material. The reaction temperature can range from 150° C. to 450° C., and is preferably from about 200° C. to 300° C. The contact time preferably ranges from about 5 to 60 seconds, and is typically about 30 seconds. Although the chlorination reaction of the present invention is usually conducted at atmospheric pressure, it may also be conducted under elevated or reduced pressure.

The chlorination reaction of the organic starting material may be conducted in any suitable reactor, such as a fixed bed reactor. It may be done in a batch or continuous mode. The reaction vessel should be constructed of materials which are resistant to the corrosive effects of hydrogen fluoride, hydrogen chloride and chlorine, such as Hastelloy® nickel alloy and Inconel® nickel alloy.

A gaseous mixture discharged from the reactor typically contains 2-chloro-1,1,1,2-tetrafluoroethane as the major product and 2,2-dichloro-1,1,1,2-tetrafluoroethane, unreacted 1,1,1,2-tetrafluoroethane, hydrogen chloride and in some cases disproportionation product(s) and/or an inert diluent. HF may be present in some embodiments of the invention. The mixture may be refined using conventional means to obtain 2-chloro-1,1,1,2-tetrafluoroethane and 2,2-dichloro-1,1,1,2-tetrafluoroethane. The recovered unreacted 1,1,1,2-tetrafluoroethane can be recycled to the reaction zone to improve the yield of 2-chloro-1,1,1,2-tetrafluoroethane. The recovered CFC-114a can be recycled to a hydrogenolysis reactor to produce additonal HFC-134a starting material.

The catalytic process of this invention provides production of HCFC-124 at significantly higher rates and/or lower temperatures than chlorination in the presence of noncatalytic materials.

Practice of the invention will become further apparent from the following non-limiting examples.

EXAMPLES

In the following illustrative examples, all parts are by weight, all percentages are molar, and all temperatures are degrees Celsius unless otherwise stated.

Preparation of HCl-Washed Carbon—Catalyst A

A commercially available carbon (102.5 g, 4×10 mesh (about 4.8×2.0 mm) granules) was soaked overnight with gentle stirring in 1M HCl. The carbon granules were collected on a fritted glass funnel, washed with deionized water and dried on the fritted glass funnel. The carbon granules were soaked a second time in 1M HCl overnight, followed by washing with deionized water and drying on the fritted glass funnel. After a third soaking in 1M HCl overnight the carbon granules were washed with deionized water until the washings were chloride free when tested with silver nitrate. The carbon granules were then dried at 110° C. for 18 hours, followed by calcination at 300° C. in air to obtain 94.7 g of dried calcined granules.

General Procedure for Chlorination

The reactor (a 0.5" (about 1.3 cm) ID, 12" (about 30.5 cm) long Inconel® nickel alloy pipe) was charged with the amount of catalyst as described in the following examples, and placed in a sand bath. The catalysts were treated and activated as described in the Examples.

The reactor effluent was sampled on-line with a Hewlett Packard HP 5890 gas chromatograph using a 20' (about 6.1 m) long, ⅛" (about 0.32 cm) diameter, column containing Krytox TM perfluorinated polyether on an inert support and a helium flow of 35 cc/minute. Gas chromatographic conditions were 70° C. for 3 min followed by temperature programming to 180° C. at a rate of 6° C./minute.

EXAMPLE 1

Chlorination Using HCl Washed Carbon Catalyst A

The general chlorination procedure described above was followed using carbon Catalyst A. The dried, acid-washed carbon catalyst (12.52 g, 30 mL of 4×10 mesh (about 4.8×2.0 mm) granules) was placed in the reactor and heated under a nitrogen flow to 350° C. over 1.5 hours. The temperature was reduced to 275° C. and the flow of chlorine started. After a half hour, the flow of $CF_3CH_2F$ (HFC-134a) was also started. Samples were taken at various times. The molar ratio of chlorine to HFC-134a was 2:1 for the 7 hour sample, 1:1 for the 1 hour, 3 hour, and 4 hour samples and 0.5:1 for the 5 hour and 6 hour samples. The contact time was 30 seconds for the 1 hour, 3 hour, 4 hour, and 7 hour samples and 40 seconds for the 5 hour and 6 hour samples. The reactor effluent was analyzed as described above. The results are shown in Table 1.

TABLE 1

| Time (hr) | Temp. (°C.) | %134a[1] | %124[2] | %114a[3] |
|---|---|---|---|---|
| 1.0 | 275 | 52.7 | 20.7 | 25.8 |
| 3.0 | 275 | 52.9 | 20.8 | 25.5 |
| 4.0 | 250 | 74.0 | 17.3 | 8.4 |
| 5.0 | 250 | 76.3 | 15.8 | 7.6 |
| 6.0 | 275 | 65.1 | 17.7 | 16.0 |
| 7.0 | 275 | 41.6 | 21.1 | 36.4 |

[1] 134a = $CF_3CH_2F$
[2] 124 = $CF_3CHClF$
[3] 114a = $CF_3CCl_2F$

Minor amounts of other products including $CF_3CH_2Cl$, $CF_3CCl_3$, $CClF_3$, and $CClF_2CClF_2$ were also found.

EXAMPLE 2

Chlorination Using 6% $LaCl_3$/Acid Washed Carbon

The general chlorination procedure described above was followed. A solution of $LaCl_3.6H_2O$ (3.46 g) in water (56 mL) was poured over 40 g of HCl-washed carbon. The resulting mixture was allowed to stand at room temperature for 1 hour with occasional stirring and was then placed in a vacuum oven at 120° C. for 18 hours to remove the water. A sample of this catalyst (14.6 g, 30 mL) was placed in the reactor and heated under a nitrogen flow to 350° C. over 1.5 hours. The temperature was reduced to 250° C. and the flows of chlorine and HFC-134a started. Samples were taken at various times. The molar ratio of chlorine to HFC-134a was 1:1 except for the 1.5 hour sample where it was 0.5:1. The contact time was 30 seconds for the 0.5 hour and 2.5 hour samples and 40 seconds for the 1.5 hour sample. The reactor effluent was analyzed as described above.

TABLE 2

| Time (hr) | Temp. (°C.) | %134a | %124 | %114a |
|---|---|---|---|---|
| 0.5 | 250 | 69.4 | 19.4 | 8.7 |
| 1.5 | 250 | 72.0 | 16.7 | 8.0 |

TABLE 2-continued

| Time (hr) | Temp. (°C.) | %134a | %124 | %114a |
|---|---|---|---|---|
| 2.5 | 275 | 49.0 | 21.6 | 25.0 |

Minor amounts of other products including $CF_3CH_2Cl$, $CF_3CCl_3$, $CClF_3$ and $CF_3CHCl_2$ were also found.

COMPARATIVE EXAMPLE A

Chlorination Using HCl-Washed Silicon Carbide

The general chlorination procedure described above was followed. A dried, acid-washed silicon carbide catalyst (48.8 g, 30 mL of 14×20 mesh (about 1.4×0.84 mm) granules) was placed in the reactor and heated under a nitrogen flow to 275° C. The flows of chlorine and HFC-134a were then started. Samples were taken at various times. The molar ratio of chlorine to HFC-134a was 2:1 for the 0.5, 1.5 and 2.5 hour samples; 1:1 for the 3.5 hour sample; and 0.5:1 for the 4.0 hour sample. The contact time was 30 seconds for the 0.5, 1.5, 2.5 and 3.5 hour samples and 40 seconds for the 4.0 hour sample. The reactor effluent was analyzed as described above. The results are shown in Table A.

TABLE A

| Time (hr) | Temp. (°C.) | %134a | %124 | %114a |
|---|---|---|---|---|
| 0.5 | 275 | 95.0 | 4.8 | 0.1 |
| 1.5 | 300 | 87.9 | 11.3 | 0.7 |
| 2.5 | 325 | 73.8 | 22.7 | 3.4 |
| 3.5 | 350 | 57.7 | 32.8 | 9.2 |
| 4.0 | 350 | 68.4 | 26.5 | 5.0 |

COMPARATIVE EXAMPLE B

Chlorination Using Shot Coke

The general chlorination procedure described above was followed. Conoco shot coke (31.0 g, 30 mL of 10×20 mesh (about 2.0×0.84 mm) granules), a highly fused petroleum coke with a surface area of 0.5 $m^2/g$, was placed in the reactor and heated under a nitrogen flow to 350° C. over 1.5 hours to remove water. The temperature was reduced to 275° C. and the flow of chlorine started. After a half hour, the flow of HFC-134a was also started. Samples were taken at various times. The molar ratio of chlorine to HFC-134a was 1:1 for all but the 4.5 hour sample where it was 2:1. The contact time was 30 seconds. The reactor effluent was analyzed as described above. The results are shown in Table B.

TABLE B

| Time (hr) | Temp. (°C.) | %134a | %124 | %114a |
|---|---|---|---|---|
| 1.0 | 275 | 97.1 | 2.8 | <0.1 |
| 2.0 | 300 | 92.9 | 6.8 | 0.2 |
| 2.5 | 300 | 90.5 | 9.0 | 0.5 |
| 3.5 | 325 | 81.8 | 16.5 | 1.6 |
| 4.5 | 350 | 62.4 | 30.3 | 7.2 |

COMPARATIVE EXAMPLE C

Chlorination Using Inconel ® Chips

The general chlorination procedure described above was followed. Inconel ® nickel alloy chips (139 g, 30 mL) were placed in the reactor and heated under a nitrogen flow to 250° C. The flows of chlorine and HFC-134a (97.3% pure) were then started. The molar ratio of chlorine to HFC-134a was 2:1 for all the samples. The contact time was 30 seconds for all the samples. The reactor effluent was analyzed as described above. The results are shown in Table C.

TABLE C

| Time (hr) | Temp. (°C.) | %134a | %124 | %114a |
|---|---|---|---|---|
| 0 | FEED | 97.3 | 2.6 | <0.1 |
| 2.0 | 250 | 98.3 | 1.6 | <0.1 |
| 4.0 | 275 | 97.0 | 3.0 | <0.1 |
| 5.0 | 300 | 92.6 | 7.1 | 0.3 |
| 6.0 | 325 | 80.0 | 18.0 | 1.9 |
| 7.0 | 350 | 56.6 | 33.4 | 9.8 |

A comparison of the results obtained in Example 1 and Example 2 with the results obtained in the Comparative Examples illustrates the accelerated chlorination of HFC-134a which can be obtained using the catalysts of this invention.

The examples serve to illustrate particular embodiments of the invention. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for producing 2-chloro-1,1,1,2-tetrafluoroethane comprising the step of: contacting gaseous 1,1,1,2-tetrafluoroethane and chlorine with a catalyst of metal halide supported on carbon at a temperature of from about 150° C. to about 450° C., wherein the metal halide is a chloride and/or fluoride of a metal selected from the group consisting of lanthanum, zinc, copper, chromium, ruthenium, rhodium, platinum, and mixtures thereof.

2. The process of claim 1 wherein the metal halide is lanthanum chloride and/or fluoride.

3. The process of claim 1 wherein the metal halide is zinc chloride and/or fluoride.

4. The process of claim 1 wherein the metal halide is copper chloride and/or fluoride.

5. The process of claim 1 wherein the metal halide is chromium chloride and/or fluoride.

6. The process of claim 1 wherein the metal halide is ruthenium chloride and/or fluoride.

7. The process of claim 1 wherein the metal halide is rhodium chloride and/or fluoride.

8. The process of claim 1 wherein the metal halide is platinum chloride and/or fluoride.

9. The process of claim 1, claim 2, claim 3, claim 4, claim 5, claim 6, claim 7, or claim 8 wherein the carbon is an acid-washed activated carbon.

10. The process of claim 1 wherein the temperature is from about 200° C. to 300° C.

11. The process of claim 1 wherein the mole ratio of chlorine to $CH_2FCF_3$ starting material is between about 0.5:1 and 10:1.

12. The process for producing 2-chloro-1,1,1,2-tetrafluoroethane comprising the step of: contacting gaseous 1,1,1,2-tetrafluorethane and chlorine with an activated carbon catalyst at a temperature of from about 150° C. to about 450° C.

13. The process of claim 12 wherein the catalyst consists essentially of carbon.

14. The process of claim 13 wherein the carbon is acid-washed.

15. The process of claim 14 wherein the ash content of the carbon is about 0.5 percent by weight, or less.

16. The process of claim 12 wherein the temperature is from about 200 to 300° C.

17. The process of claim 12 wherein the mole ratio of chlorine to $CH_2FCF_3$ starting material is between about 0.5:1 and 10:1.

* * * * *